United States Patent
Szkulmowski et al.

(10) Patent No.: US 12,270,983 B2
(45) Date of Patent: Apr. 8, 2025

(54) METHOD AND APPARATUS FOR DETERMINATION OF A TRAJECTORY AND IMAGING DEVICE

(71) Applicant: Inoko Vision Spółka z ograniczon odpowiedzialnościa, Torun (PL)

(72) Inventors: Maciej Szkulmowski, Torun (PL); Krzysztof Dalasinski, Torun (PL); Michal Meina, Torun (PL); Maciej Nowakowski, Torun (PL); Krystian Wrobel, Torun (PL); Maciej Bartuzel, Pszenno (PL); Szymon Tamborski, Torun (PL); Patrycjusz Stremplewski, Torun (PL)

(73) Assignee: Inoko Vision Spółka z ograniczon odpowiedzialnościa, Torun (PL)

( * ) Notice: Subject to any disclaimer, the term of this patent is extended or adjusted under 35 U.S.C. 154(b) by 324 days.

(21) Appl. No.: 17/794,579

(22) PCT Filed: Jan. 29, 2021

(86) PCT No.: PCT/IB2021/050732
§ 371 (c)(1),
(2) Date: Jul. 21, 2022

(87) PCT Pub. No.: WO2021/152537
PCT Pub. Date: Aug. 5, 2021

(65) Prior Publication Data
US 2023/0147006 A1    May 11, 2023

(30) Foreign Application Priority Data
Jan. 29, 2020 (EP) .................................... 20154381

(51) Int. Cl.
*G06T 19/20* (2011.01)
*G02B 21/36* (2006.01)

(52) U.S. Cl.
CPC .. *G02B 21/367* (2013.01); *G06T 2207/20221* (2013.01)

(58) Field of Classification Search
USPC ................. 128/920, 922–925; 382/103–128, 382/151–159; 706/1–62, 900–903
See application file for complete search history.

(56) References Cited

U.S. PATENT DOCUMENTS 8,970,495 B1 * 3/2015 Biffle ..................... G09G 3/003
345/158
9,775,512 B1 * 10/2017 Tyler ...................... G06V 40/19
(Continued)

FOREIGN PATENT DOCUMENTS

| WO | WO2013125547 | 8/2013 |
| WO | WO2016115203 | 7/2016 |
| WO | WO2018017751 | 1/2018 |

OTHER PUBLICATIONS

Thompson Ben; Stimulus and Eye Tracking System; 2018 (Year: 2018).*

(Continued)

*Primary Examiner* — Marcellus J Augustin
(74) *Attorney, Agent, or Firm* — Soody Tronson; STLG Law Firm (57) ABSTRACT

A method of determination of a trajectory of a living tissue, in which subsequent frames representing images of living tissue are acquired with at least a first imaging device and at least a first segment of a trajectory of the living tissue is determined with a use of relative displacements of at least first subset of subsequent frames and recalculation thereof to coordinates corresponding to time of frame acquisition to form a vector Tm elements tm wherein element tm is at least (Continued)

one coordinate of living tissue, element tm of vector Tm is determined with a use of relative displacements $p_{m,k}$ of at least two preceding frames.

20 Claims, 5 Drawing Sheets

(56) References Cited

U.S. PATENT DOCUMENTS

| | | | | |
|---|---|---|---|---|
| 11,490,809 | B2* | 11/2022 | Krueger | G06F 3/013 |
| 11,762,461 | B2* | 9/2023 | Young | G06F 3/013 706/45 |
| 2016/0066781 | A1* | 3/2016 | Thompson | A61B 3/113 351/209 |
| 2016/0210497 | A1* | 7/2016 | Rougeaux | G06F 3/013 |
| 2020/0305708 | A1* | 10/2020 | Krueger | G06F 3/013 |

OTHER PUBLICATIONS

Zizi Martin; Unique Patterns Extracted From Involuntary Eye Motions to Identify Individuals; 2018 (Year: 2018).*
Popovich Milan Momcilo; Holographic Waveguide Optical Tracker; 2017 (Year: 2017).*
Anthony Brian W; Circular Scanning Technique for Large Area Inspection (Year: 2016).*
Unique Patterns Extracted From Involuntary Eye Motions to Identify Individuals (Year: 2018).*
Circular Scanning Technique for Large Area Inspection (Year: 2016).*
Holographic Waveguide Optical Tracker (Year: 2017).*
Stimulus and Eye Tracking System (Year: 2018).*
WO2021152537 International Search Report and Written Opinion of the International Searching Authority.

* cited by examiner

METHOD AND APPARATUS FOR DETERMINATION OF A TRAJECTORY AND IMAGING DEVICE

The invention concerns a method of determination of a trajectory of a living tissue, apparatus therefor, computer program product therefore and a living tissue imaging system using said apparatus.

Imaging of living tissue is prone to errors and distortions caused by uncontrollable movements of tissue during image acquisition. Acquisition of detailed image takes time long enough for living tissue e.g. eye to make a move considerably longer than desired spatial resolution. The problem is known in the art and is partially solved by either real time tracking of the imaged tissue or determining tissue trajectory and compensation in image post processing.

U.S. Pat. No. 9,867,538 discloses a method for robust eye tracking and ophthalmologic apparatus therefor. An ophthalmic apparatus includes an adaptive optics scanning laser ophthalmoscopy (AOSLO) apparatus, a wide field of view scanning light ophthalmoscopy (WFSLO) apparatus, and a tracking processor that controls a tracking mirror based on position information calculated from AOSLO and WFSLO images. In another embodiment, the tracking processor controls the tracking mirror based on position information calculated from WFSLO images only. Depending on the amount of movement a target image with respect to a reference image, and the accuracy of detection thereof, the tracking mirror of either the AOSLO apparatus or the WFSLO apparatus can be selectively controlled according to a difference in position of the target image with respect to the reference image.

US patent application no US20150077706A1 discloses Real-time optical and digital image stabilization for adaptive optics scanning ophthalmoscopy. A real-time ophthalmoscope system for imaging an eye includes a wide field scanning laser ophthalmoscope (SLO) configured for wide field imaging of the eye. The system also includes a small field SLO configured for high resolution imaging of the eye. A 2D tracking mirror electrically coupled to a computer, and a 2D steering mirror electrically coupled to the computer, are both disposed in an optical path between the small field SLO and the eye. The system is configured to acquire a plurality of small field images at a plurality of locations on the eye as defined by the 2D steering mirror, each of the small field images is stabilized for a motion of the eye by the 2D tracking mirror. A method for imaging of the eye is also described.

US patent application US2016066781 discloses a method of extracting eye velocity information from a video footage having a plurality of frames, comprising detecting at least part of an eye in at least two frames of the video footage, applying an optical flow algorithm to the at least two frames of the video footage to extract pixel velocity information, and determining a statistical measure from the pixel velocity information within the detected at least part of the eye. It further discloses a method of extracting head image trajectory information from a video footage having a plurality of frames, comprising detecting at least part of a facial region of the head image in at least two frames of the video footage, determining a measure of the movement of the at least part of a facial region between the at least two frames, and determining a transformation map from the measure of the movement. It is suitable for use with video footage of RGB images (1920 by 1080 pixels) at 25 frames per second. It discloses use of camera rates of 30 Hz and 25 Hz. Methods according to D1 operates on pixel by pixel basis and aim to determine pixel velocity. Generally high resolution imaging devices used conventionally for eye imaging are too slow to be used for reliable determination of the trajectory of living tissue with respect to image sequence and motion compensation techniques are not fully effective. Another drawback of known image-based approaches is their dependence on the chosen reference frame, which by itself could be distorted by motion artifacts. Algorithms have been proposed to correct these artifacts in the reference frame however, such approaches are not free of limitations. For instance, the algorithms may lack ground truth reconstruction validation.

Known methods for determination of trajectory use reference frames and therefore are susceptible to random errors caused by unexpected movements exceeding assumed range of speed and amplitude or would require over scaled hardware to capture frames fast enough and large enough.

The aim of the invention is to provide a method and the system for accurate determination of a trajectory of living tissue subjected to voluntary and involuntary movements therefore enabling analysis of movements and compensation in post processing of the images recorded with high resolution imaging device.

The invention concerns a method of determination of a trajectory of a living tissue, in which subsequent frames representing images of living tissue are acquired with at least a first imaging device and at least a first segment of a trajectory of the living tissue is determined with a use of relative displacements of at least first subset of subsequent frames and recalculation thereof to coordinates corresponding to time of frame acquisition to form a vector Tm elements tm. Element tm is at least one coordinate of living tissue. Element tm of vector Tm is determined with a use of relative displacements $p_{m,a}$, $p_{m,b}$ of at least two preceding frames and relative displacements $p_{m,a}$, $p_{m,b}$ are determined using predetermined criterion. Frame acquisition rate of the first imaging device is at least 500 FPS. Frame size acquired from the first imaging device is at least 1000 pixels. Field of view of the first imaging device is at least 1° in X plane and Y plane. That combination of parameters of the first imaging device proved to be feasible and sufficient to provide frames adequate for successful trajectory reconstruction of living tissue. Use of multiple previous frames allows error reduction e.g. by averaging. Experiments showed advantageous results for field of view within a range of 1°÷4°. Upper limitation made it easier to provide sufficient sensitivity to high velocity tissue motion.

Advantageously at least a second subset of frames is used to calculate alignment frames corresponding to both first and second segment and using distances between alignment frames to minimize cumulative error by recalculation of relative displacement between elements of trajectory in the first and the second segment.

Advantageously alignment frames are acquired with the first imaging device. Preferably trajectory is analyzed to detect a loop and identify alignment frames as frames contained in at least two segments of trajectory.

Alternatively alignment frames are obtained with a second imaging device.

The invention further concerns an apparatus for determination of a trajectory of a movement of a living tissue, having a first imaging device and processing unit. The first imaging device is adapted to acquire subsequent frames with frame acquisition rate of at least 500 FPS, frame size of at least 1000 pixels and field of view of at least 1° in X plane and Y plane. The processing unit is adapted to execute a method according to the invention.

The invention further concerns a computer program product for determination of trajectory of a living tissue, which when run on processing unit fed with subsequent frames comprising at least a subset of frames acquired with frame acquisition rate of at least 500 FPS, frame size of at least 1000 pixels and field of view of at least 1° in both X plane and Y plane.

The invention further concerns imaging system comprising a second imaging device for a living tissue characterized in that it further comprises an apparatus for determination of a trajectory of a living tissue according to the invention and is adapted to reposition images acquired with the second imaging device to compensate movement of the living tissue. Thus synergistic effect of motion compensation and aid in trajectory determination is obtained.

Processing unit of the apparatus for determination of a trajectory of a living tissue advantageously is adapted to receive frames from the second imaging device and to use as alignment frames.

The invention has been described below in detail, with reference to the following figures wherein.

EMBODIMENTS OF THE INVENTION

Figure 1:
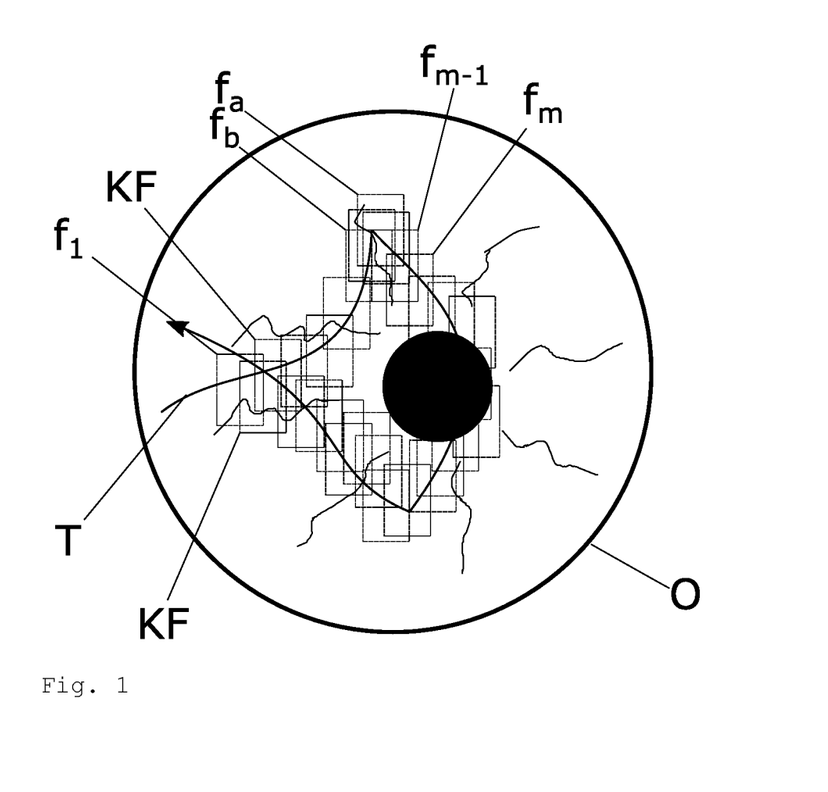
FIG. 1 shows schematically frames and areas along the trajectory.

FIG. 1 shows schematically an eye and frames acquired with imaging device FET. Subsequent frames are in different locations due to eye movements. Trajectory of the frames in eye coordinate system is exactly complementary to trajectory of an eye in the imaging device FET coordinate system. Therefore determination of frame is the same operation as determination the trajectory of eye living tissue in imaging device coordinate system—those two trajectories differ only in sign.

Figure 2A:
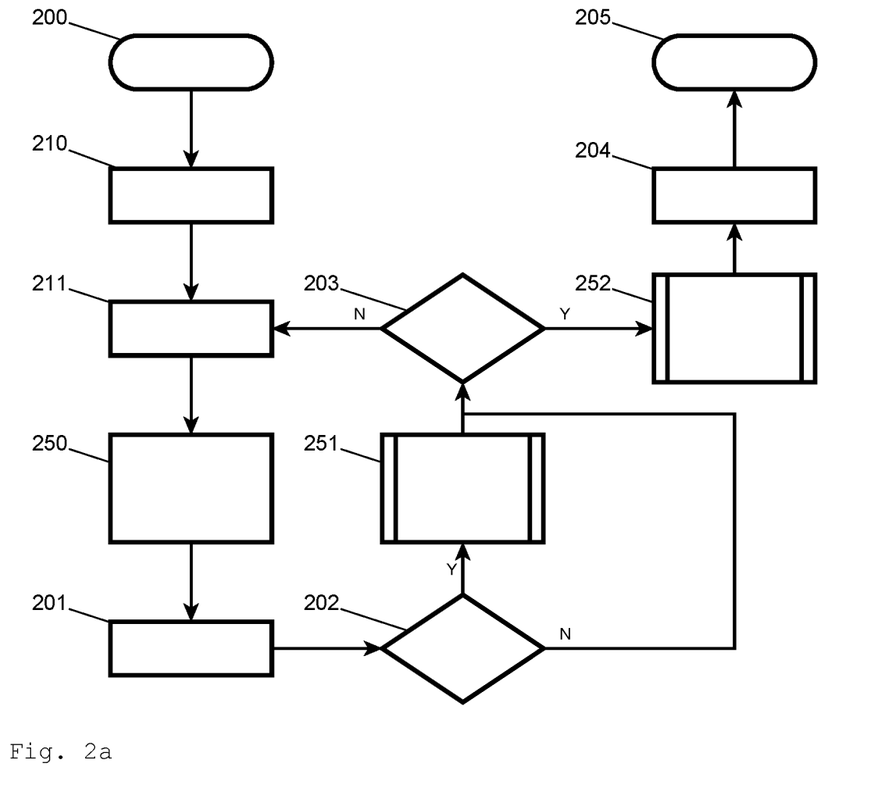
FIG. 2a presents a flowchart of an embodiment of the method according to the invention.

A flow chart of an example of the method according to the invention is shown in FIG. 2a. The method of determination of a trajectory T of a living tissue O, is in this example applied to an eye. Movements of the eye ball are among the fastest in the body, and therefore, the method of determination of trajectory is applicable to determination of trajectories of other organs. Eyeball in the setup discussed below can move 1000°/s—that contributes to 300 mm/s for an average eye.

Frames of the eye are acquired with the first imaging device FET with frame acquisition rate of 1240 FPS. The field of view was set to 3.37°×3.24°. The imaging beam diameter at the cornea was equal to 1.96 mm. The theoretical on-axis beam size on the retina in this case was 8.5 µm. The confocality of the system was deliberately sacrificed to gain sensitivity by using a 100-µm pinhole. The airy disc diameter at the detection plane was 36.4 µm. The confocality described in terms of times-diffraction-limited spot size was equal to 2.75 and frame size was accordingly 4432 pixels (140×140 pixels).

Further studies have shown that reliable trajectories can be obtained with frame rate as low as 500 FPS and frame size as low as 1000 px. Naturally higher frame rates and larger frames allow more accurate determination of trajectory.

First imaging device delivered subsequent frames including F1, Fa, Fb, Fm. Frames represent images of small parts of eye. The relation between frame rate and frame size contributes to a result where every frame is a part of subset of subsequent frames.

According to the method positions of the frames in the said subset of frames relative to the position of at least first area is determined—like in a state of the art methods with that difference that reference frame is not selected.

Said positions are thereafter recalculated to sets of coordinates (points) forming at least the first segment of trajectory T corresponding to time of acquisition. Sets of coordinates form a vector Tm elements tm wherein element tm is a point of trajectory represented as a set of two coordinates:

$$t_m = \{x_m, y_m\} \tag{1}$$

and corresponding to a single frame $f_m$.

Figure 2B:
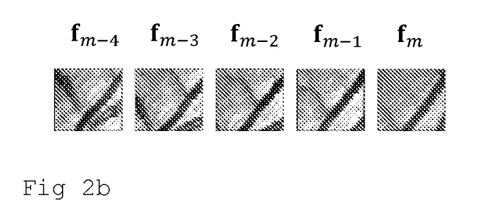
FIG. 2b illustrates displacements between a frame and previous frames.
Figure 2C:
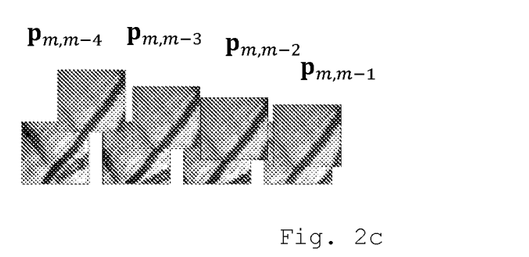
FIG. 2c illustrates displacements between a frame and previous frames.

In the present example the trajectory reconstruction algorithm operates in two stages. In the first stage, the retinal trajectory is estimated by the so-called N-back algorithm, in which each new frame is aligned against n previous frames as shown in FIG. 2b and FIG. 2c. In the second stage, cumulative errors in the trajectory reconstructed in the first stage are corrected.

After start 200 of the process a first frame f1 is retrieved in acquisition step 200. It involves scanning and recalculation of pattern to the obtain rectangular frame as described in more detail below.

Further frames are repeatedly retrieved in acquisition step 211.

A new trajectory point of the retina was estimated by estimating 250 the displacements between the frame incoming in acquisition step 211 and a subset of the ones acquired earlier. These displacements are added to the trajectory points found for the latter frames. In the simplest case, the displacement from only one previous frame was considered, which is noted as follows:

$$t_m = t_{m-1} + p_{m,m-1} \tag{2}$$

where $t_m = \{x_m, y_m\}$ is the trajectory point in Euclidean space, m is the iterator of frames/trajectory points and $p_{m,m-1}$ denotes the displacement between frames m and m−1. Displacements are shown in FIG. 2c. Formally, for frames a, b $p_{a,b}$ is estimated by minimizing a criterion function that measures the alignment of frames $f_a$ to $f_b$. Various criteria could be employed interchangeably based on the hardware requirements and computation latency needed. In this example, the enhanced correlation coefficient (ECC) disclosed in Evangelidis, Georgios D., and Emmanouil Z. Psarakis. "Parametric image alignment using enhanced correlation coefficient maximization." IEEE Transactions on Pattern Analysis and Machine Intelligence 30.10 (2008): 1858-1865 was used, as it can provide sub-pixel precision and gradient descent-based computation can be run on a CPU. Naturally person skilled in the art can easily suggest and implement other applicable criterions for estimation of frame distance.

The accuracy and resistance to noise of the simple trajectory building algorithm, is increased in the N-back version of the algorithm, by calculating the displacement of the new frame from N previously acquired frames and averaging them:

$$t_m = \frac{1}{N}\sum_{n\in B}(t_{m-n} + p_{m,m-n}) \quad (3)$$

where n represents indices of frames calculated in reference to the newly acquired frame (i.e. n=1 denotes the frame that directly precedes the new frame). Using trial-and-error experiments, a set $B \in \{1,2,4,8,16,32,128,256,512\}$ of the frame indices was chosen. In this way, the method compares not only consecutive frames but also tries to align frames that were acquired almost half a second earlier. If the criterion $D(f_a, f_b)$ cannot be calculated due to low SNR or a displacement exceeding the size of the frames, the corresponding index n, is removed from set B. N represents the total number of frames in the set B. After calculations frame fm is added 202 to the subset of frames used to determine following points of trajectory. Averaging allows reduction of error. A person skilled in the art may find a different composition of frames indices B that will maximize the efficiency of the method in terms of computation speed and required accuracy.

The alignment of frames described above is prone to small errors in $p_{a,b}$ that will propagate in $t_m$ over time. Due to the recursive nature of the method, the trajectory estimation error can be modeled as a random walk process, which leads to the conclusion that the ideally calibrated system has non-stationary zero mean error, with the error's variance growing linearly with time—meaning that errors have tendency to cumulate.

Figure 5A:
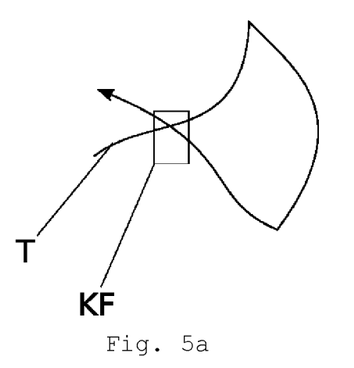
FIG. 5a-d show various loops of trajectory.
Figure 5B:
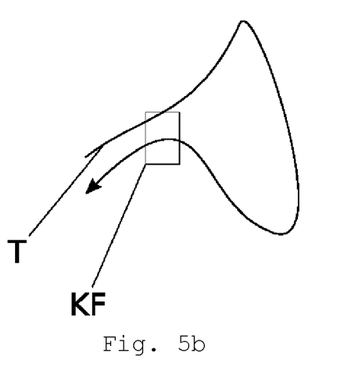
Figure 5C:
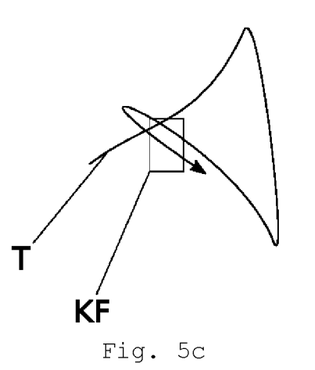
Figure 5D:
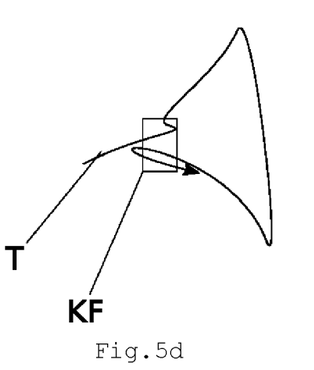

In order to correct this non-stationary error, an additional technique can be applied. It exploits the fact that the eye returns from time to time to the same location and the error accumulated by Eqs. 2-3 can be corrected by a new displacement calculation. The technique introduces alignment (or key) frames KF, which can be intuitively understood as a subset of all frames in the acquired dataset with translations $p_{a,b}^{KF}$ that can be calculated, for frames $f_a$ and $f_b$ in close spatial locations on the retina, independent of time separation. Practically alignment frames can be detected 202 by detection of loops or intersections of the trajectory T in real time or in post processing. Alignment frame allow to minimize cumulative error by correction of the trajectory 251. Examples of loops with intersections are given in FIG. 5a and FIG. 5c and examples of loops without intersections are given in FIG. 5b and FIG. 5d. As long as two nonadjacent segments of trajectory T can be observed in the same frame this frame can be used as alignment frame KF.

Formally, these corrections for KF can be performed using the multidimensional scaling (MDS) mathematical framework disclosed in I. Borg, and P. Groenen. "Modern multidimensional scaling: Theory and applications." Journal of Educational Measurement 40.3 (2003): 277-280, in which distances between KF are used to correct all the trajectory points from the first stage. In other words, a matrix $P^{KF}$ is constructed with all translation distances, $|p_{a,b}^{KF}|$, between the KF that can be calculated. A trajectory $\hat{T}^{KF}$ is found by minimizing a stress function, $\sigma$, with respect to the KF positions, $\hat{T}^{KF}=[\hat{t}_1^{KF}, \hat{t}_2^{KF}, \hat{t}_3^{KF}, \ldots]$.

$$\sigma(\hat{T}^{KF})=\Sigma_{a<b}w_{a,b}(P_{a,b}^{KF}-|\hat{t}_a^{KF}-\hat{t}_b^{KF}|) \quad (4)$$

where $P_{a,b}^{KF}=|p_{a,b}^{KF}|$ are distance computed between an a-th and b-th alignment frame and $w_{a,b}$ is a weight that indices missing or imputed values. Naturally person skilled in the art can suggest alternative scheme for cumulative error minimization using alignment frames—possibly suboptimal but still operational.

The alignment frame trajectory, $T^{KF}$, has an inherently low sampling rate, but has theoretically zero non-stationary errors. The final retinal trajectory, $T^{FET}$, is estimated by casting the N-back trajectory, T, on the alignment frame trajectory, $T^{KF}$, exploiting the interpolation for trajectory points in between the alignment frames.

Accordingly if alignment frame is detected in step 202 trajectory is corrected in step 251.

After end of tracking 203 corrected trajectory is output in step 204 and algorithm is terminated 205.

The method is easily implemented in computer program product run on a processing unit fed with frames in real time or offline processing. The former has an advantage of backward recalculation of the whole trajectory in step 252 after end of tracking 203.

Alignment frames can alternatively by obtained from the second imaging device offering slower frame rate and higher resolution. Such device can provide alignment frames corresponding to whole trajectory or at least its larger parts. It is a specially advantageous when method of determination of trajectory together with first imaging device FET is to be integrated with other imaging system such as WFSLO.

Figure 3:
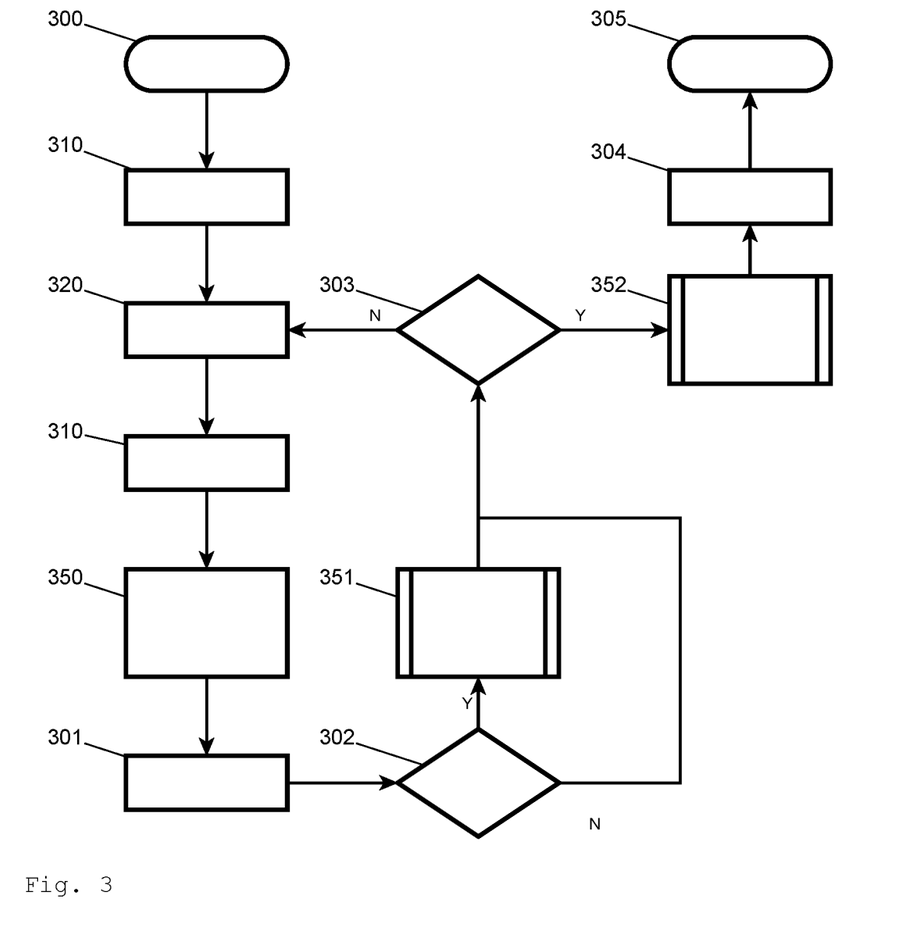
FIG. 3 presents a flowchart of an another embodiment to the method according to the invention.

A block diagram of an example of such embodiment of the invention is shown in FIG. 3. After start 300 a frame from first imaging device is acquired 301 then within a loop the WFSLO is used to obtain an image of the living tissue in a strip-by-strip manner. In-between the strips of WFSLO subsequent frames are acquired with the first imaging device in acquisition step 310.

Displacements $p_{a,b}$ are calculated in the same manner as in the previous examples and frames already used are added to the pool for subsequent frames in step 301.

The difference consists in that in step 302 it is determined weather part of image already acquired with WFSLO can be used as alignment frame and if it is the case trajectory is corrected in step 351. After end of tracking 303 whole trajectory may be optionally recalculated 352 and output 304. Afterwards the process finishes 305.

It should be stressed that determination of trajectory without minimization of cumulative error is still useful in some applications especially the ones where it is a speed of human tissue that is crucial—eg. for online image stabilization to prevent motion artifacts in the obtained images that would cause image artifacts impossible to correct in post-processing with optical angiography being one of the possible examples.

Figure 4A:
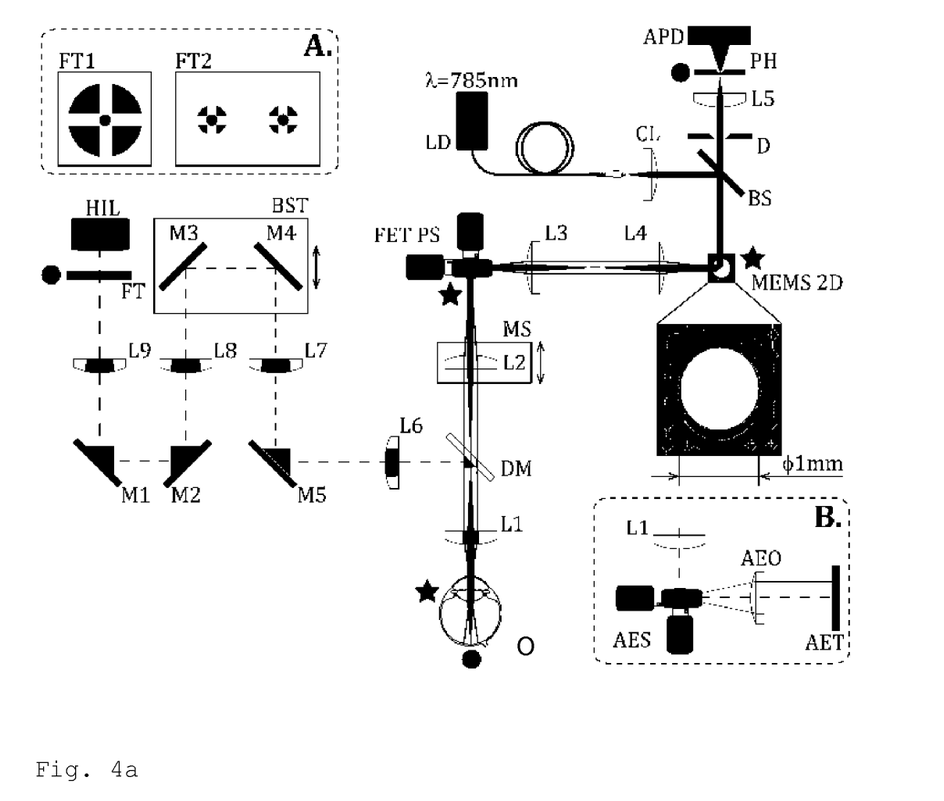
FIG. 4a presents a block diagram of imaging device applicable for use in the system according to the invention and a method according to the invention.
Figure 4B:
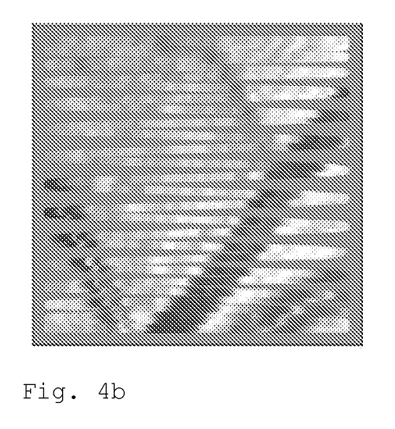
FIG. 4b illustrates Lissajous scanning pattern.

A block diagram of a device FET applicable to use in the method according to the invention is shown in FIG. 4a. LD represents laser diode; CL represents a collimating lens; BS represents pellicle beamsplitter; L1-L9 represent achromatic doublets; MEMS 2D represents two-axis resonant MEMS scanning mirror; FET PS represents positioning galvanometric mirrors; D represents regulated iris aperture; PH represents pinhole; APD represents avalanche photodiode; HIL represents halogenic illumination lamp, BST represents Badal stage, AES represents artificial eye scanners set, AEO represents artificial eye objective, AET represents artificial eye test target. Stars and circles denote conjugated planes. Inset A: Targets used for in vivo experiments. Diameter of FT1 subtends 1.5° on the retina and was used for the experiment with static fixation. FT2 was used for the experiments with saccades; the diameters subtend 0.6° and the distance between the centers ranged from 1-8°. Inset B: artificial eye attachable to the system for testing.

The illumination source for this scheme is a 785-nm laser diode LD coupled with a single-mode fiber and collimated to a beam diameter of 0.7 mm by an aspherical lens CL. A pellicle beamsplitter BS reflects the beam and directs it onto a scanning mirror 2D MEMS with 1-mm active aperture, based on the microelectromechanical system (MEMS) technology. After reflecting off the scanning mirror, the beam passes through a telescope system composed of lenses L4 and L3.

The MEMS 2D scanning mirror was set to its maximum frequency, which resulted in a Lissajous scanning pattern, as shown in FIG. 4a. Therefore, to obtain frames in the first step, the raw images acquired by the detector APD needed to be resampled, to form the uniformly sampled rectangular images shown in FIG. 3b. This step was performed with a sparse matrix by dense vector multiplication $f=M \cdot f^L$. $f^L = [f_1^L, f_2^L, \ldots, f_K^L]$ represents intensity data vector acquired directly by APD. $f_i^L$ is single APD reading. Resulting frame f is a N×N rectangular image organized in a single row-by-row vector of size $N^2$. Resampling matrix M is a sparse matrix of size $N^2 \times K$, constructed from the Lissajous coordinates in a a way that each row of M has a non-zero elements at indices that correspond to the s-closest distance between the Lissajous coordinates and the coordinates in the resulting frame f.

Person skilled in the art is able to offer a number of alternative constructions of the FET imaging device once learning the teaching of the present description that it has to provide frame acquisition rate of at least 500 FPS and frame size N×N of at least 1000 pixels and field of view of at least 1 deg.

FET device was tested in a system's including tracking performance with a use of a simplified artificial eye composed of X-Y galvanometric scanners set GVSC, imaging lens AEO, and test target AET was installed in the setup as shown in FIG. 4a. The imaging lens was chosen to be the same as L1 and arranged in a 4f system, in order to maintain the same scanning angles. The scanners were positioned in the eye pupil plane, and a voltage-to-optical-angle calibration was performed using the USAF 1951 test target. For tracking validation, a printed fundus image was used as the test target. The image was prepared in a way that allowed to obtain images, which resemble the ones from a preliminary study done in vivo with human eyes.

Figure 4C:
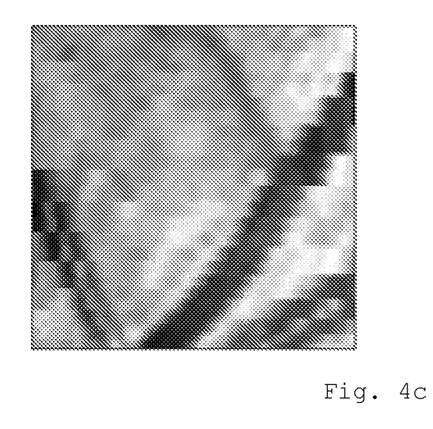
FIG. 4c shows reconstructed rectangular frame from the scanned points.
Figure 4D:
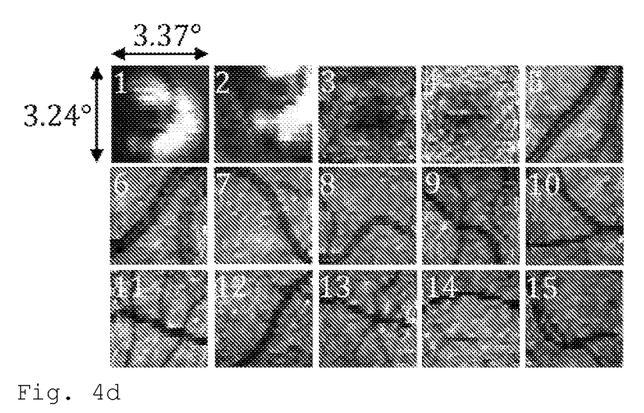
FIG. 4d shows exemplary frames acquired with the first imaging device.

FIG. 4c shows frame reconstructed after Lissajous scanning. FIG. 4d shows frames acquired with field of vie 3.27°×3.24°. Frames 1-2 show part of an optic nerve, frames 3-4 show fovea; frames 5-15 show retinal vasculature with different sizes. Other experiments showed that tracking works for field of view as low as 1 degree in both planes.

Addition of apparatus according to the invention to the scanning laser ophthalmoscope known in the art allows simultaneous imaging and tracking trajectory of living human eye. Knowledge of the trajectory of the eye enables compensation of said movement in resulting images and consequently stabilization. It can either be done in real time or in post-processing.

It is stressed that the above-mentioned embodiments illustrate rather than limit the inventions, and that person skilled in the art will be able to design many alternative embodiments.

As one the inventions claimed is also a computer program product for running on a processing unit, at least including code portions for performing steps of a method according to the invention. The computer program may consist of or include or more of: a subroutine, a function, a procedure, a class, an object method, an object implementation, an executable application, an applet, a servlet, a source code, an object code, a shared library/dynamic load library and/or other sequence of instructions designed for execution on a programmable apparatus. The computer program may be provided on a data carrier, such as a CD-type optical disc, a DVD-type optical disc, a hard disk, or diskette, stored with data loadable in a memory of a computer system, the data representing the computer program. The data carrier may thus be a tangible data carrier. The data carrier may be a data connection, such as a telephone cable or a network cable. The data carrier may further be a non-tangible data carrier such as a wireless connection.

In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. Use of numerals "first", "second" and further by the name of elements does not introduce particular order but merely provides a way of distinction. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

It is a particular advantage of the method according to the invention that no reference frame is used but instead trajectory with respect to a number of frames is observed. That approach allows better and more reliable analysis of eye trajectory and velocity. Analysis of eye movement is in turn applicable in diagnosis of some neurodegenerative diseases including multiple sclerosis, Parkinson disease, Alzheimer disease, ataxias, strokes, palsies and others. It is also useful in diagnosis of diabetes, hypertension and others.

Knowledge of exact position and prediction of movement of living tissue is crucial in surgical operations especially with use of manipulators and robotics. Therefore although eyes were much emphasized in the description above the invention is applicable for determining trajectory of numerous human organs including muscles, especially heart but also bladder, liver, kidney ovaries, pancreas, thymus, trachea and others.

Specific patterns in movements of tissue is also applicable in biometry.

The invention claimed is:

1. A method for determining a trajectory and controlling a position of a living tissue, the method comprising:
   acquiring subsequent frames representing images of the living tissue by a first imaging device having a frame acquisition rate of at least 500 FPS and a frame size of at least 1000 pixels and a field of view of at least 1° in X plane and Y plane;
   determining, by a processing unit, at least a first segment of the trajectory of the living tissue using relative displacements of at least a first subset of subsequent frames;
   recalculating, by the processing unit, the relative displacements to coordinates corresponding to time of frame acquisition to form a vector Tm of elements tm, wherein element tm is at least one coordinate of the living; and
   controlling, by the processing unit, a movement of the living tissue based on the determined trajectory.

2. The method according to claim 1, further comprising:
using at least a second subset of frames to calculate alignment frames corresponding to the at least first segment and at least a second segment of the trajectory.

3. The method according to the claim 2, wherein the alignment frames are acquired with the first imaging device.

4. The method according to claim 3, further comprising: detecting a loop in the trajectory wherein at least two non-adjacent segments are in proximity with each other; and
identifying alignment frames contained in the at least two non-adjacent segments.

5. Method according to claim 2, wherein the alignment frames are obtained with a second imaging apparatus.

6. The method according to claim 1, further comprising repositioning, by an imaging system, images acquired with the first imaging device, to compensate for the movement of the living tissue.

7. The method according to claim 1, further comprising acquiring images of the living tissue with a second imaging device.

8. The method according to claim 7, further comprising repositioning, by an imaging system, images acquired with either the first imaging device or the second imaging device, to compensate for the movement of the living tissue.

9. The method of claim 1, wherein controlling the movement of the living tissue comprises adjusting a position of the living tissue to maintain a desired trajectory.

10. The method of claim 1, wherein the adjusting of the position of the living tissue to maintain a desired trajectory is achieved by moving the tissue with respect to the imaging device, moving the imaging device with respect to the tissue, or a combination of both.

11. A device for determining a trajectory of a movement and controlling of a living tissue, comprising:
a first imaging apparatus adapted to acquire subsequent frames with a frame acquisition rate of at least 500 FPS, and frame size of at least 1000 pixels and a field of view of at least 1° in X plane and Y plane; and
a processing unit, adapted to execute a method comprising:
determining at least a first segment of the trajectory of the living tissue using relative displacements of at least a first subset of subsequent frames;
recalculating the relative displacements to coordinates corresponding to time of frame acquisition to form a vector Tm of elements tm wherein element tm is at least one coordinate of the living tissue;
controlling a movement of the living tissue based on the determined trajectory; and
repositioning images acquired with a second imaging device to compensate for the movement of the living tissue.

12. The device of claim 11, wherein the device is configured to use at least a second subset of subsequent frames to calculate alignment frames corresponding to the at least first segment and at least a second segment.

13. The device of claim 12, wherein the alignment frames are acquired with the first imaging apparatus.

14. The device of claim 11, further comprising a second imaging apparatus configured to reposition images acquired with the second imaging apparatus to compensate for movement of the living tissue.

15. The device of claim 14, wherein the processing unit is configured to receive frames from the second imaging device to use as alignment frames.

16. The device of claim 11, wherein controlling the movement of the living tissue comprises adjusting a position of the living tissue to maintain a desired trajectory.

17. The device of claim 11, wherein the adjusting of the position of the living tissue to maintain a desired trajectory is achieved by moving the tissue with respect to the imaging device, moving the imaging device with respect to the tissue, or a combination of both.

18. A non-transitory computer readable medium having a computer program product for determining a trajectory and controlling the position of a living tissue, the computer product program comprising computer-readable instructions that when executed by a processing unit coupled to at least one memory device, cause the processing unit to perform a method comprising:
acquiring subsequent frames representing images of the living tissue with the first imaging apparatus having a frame acquisition rate of at least 500 frames per second (FPS), a frame size of at least 1000 pixels, and a field of view of at least 1° in both X and Y planes; and
determining at least a first segment of the trajectory of the living tissue using relative displacements of at least a first subset of subsequent frames;
recalculating the relative displacements to coordinates corresponding to a time of frame acquisition to form a vector of elements, wherein each element is at least one coordinate of the living tissue;
controlling a movement of the living tissue based on the determined trajectory; and
repositioning images acquired with a second imaging device to compensate for the movement of the living tissue.

19. The non-transitory computer-readable medium of claim 18, wherein the method further comprises: using at least a second subset of the subsequent frames to calculate alignment frames corresponding to the at least first segment and at least a second segment.

20. The non-transitory computer-readable medium of claim 19, wherein the method further comprises minimizing a cumulative error in determining the trajectory of the living tissue by recalculating relative displacement between elements of the trajectory in the at least first segment and the at least second segment.

* * * * *